(12) United States Patent
Gregoire et al.

(10) Patent No.: US 11,202,623 B2
(45) Date of Patent: Dec. 21, 2021

(54) SUTURE PASSER

(71) Applicant: ArthroCare Corporation, Austin, TX (US)

(72) Inventors: David Gregoire, Mission Viejo, CA (US); George W. White, Corona, CA (US)

(73) Assignee: ArthroCare Corporation, Austin, TX (US)

( * ) Notice: Subject to any disclaimer, the term of this patent is extended or adjusted under 35 U.S.C. 154(b) by 265 days.

(21) Appl. No.: 16/460,045

(22) Filed: Jul. 2, 2019

(65) Prior Publication Data

US 2019/0321029 A1 Oct. 24, 2019

Related U.S. Application Data

(63) Continuation of application No. 14/962,178, filed on Dec. 8, 2015, now Pat. No. 10,383,621, which is a continuation of application No. 12/619,124, filed on Nov. 16, 2009, now Pat. No. 9,211,118.

(51) Int. Cl.
*A61B 17/04* (2006.01)
*A61B 17/29* (2006.01)
*A61B 17/06* (2006.01)

(52) U.S. Cl.
CPC ...... *A61B 17/0469* (2013.01); *A61B 17/0483* (2013.01); *A61B 17/29* (2013.01); *A61B 2017/06042* (2013.01)

(58) Field of Classification Search
CPC . A61B 17/0625; A61B 17/29; A61B 17/0483; A61B 17/0469; A61B 2017/06014; A61B 2017/06042

See application file for complete search history.

(56) References Cited

U.S. PATENT DOCUMENTS

| | | | | |
|---|---|---|---|---|
| 3,842,840 A | * | 10/1974 | Schweizer | A61B 17/04 606/145 |
| 7,758,597 B1 | * | 7/2010 | Tran | A61B 17/0469 606/144 |
| 2003/0065337 A1 | * | 4/2003 | Topper | A61B 17/0625 606/144 |

* cited by examiner

*Primary Examiner* — Diane D Yabut
*Assistant Examiner* — Christina C Lauer
(74) *Attorney, Agent, or Firm* — Norman F. Hainer, Jr.

(57) ABSTRACT

A suturing device for grasping soft tissue and placing stitches in soft tissue during endoscopic procedures is described. An elongate housing with a stationary jaw and a movable jaw disposed at the distal end are configured for grasping and releasing soft tissue. A movable needle disposed within the housing is actuated to engage a length of suture and drive the suture into and through the grasped soft tissue. A suture capture member is disposed on the movable jaw and is configured to allow passage of the needle therethrough while securing a portion of the stitched length of suture.

19 Claims, 7 Drawing Sheets

SUTURE PASSER

CROSS-REFERENCE TO RELATED APPLICATIONS

This application is a continuation of U.S. patent application Ser. No. 14/962,178 filed Dec. 8, 2015, which is a continuation of U.S. patent application Ser. No. 12/619,124, filed Nov. 16, 2009, now U.S. Pat. No. 9,211,118 issued Dec. 15, 2015, which is incorporated by reference herein.

FIELD OF THE DISCLOSURE

The present invention relates to a method and apparatus for placing sutures in soft tissue. More particularly, the present invention relates to apparatus and methods improve the ability to place a stitch or suture deeper within tissue when compared to conventional methods. Although methods and devices described herein make reference to arthroscopic repair of torn rotator cuffs, the principles of the devices and methods may be applied to any soft tissue application.

BACKGROUND

Traditional suturing of body tissues is a time consuming aspect of most surgical procedures. Many surgical procedures are currently being performed where it is necessary to make a large opening to expose the area of, for instance, the human body that requires surgical repair. In recent practice, endoscopes are used to allow the viewing of certain areas of the body through a small puncture wound without exposing the entire body cavity. Endoscopes can be used in conjunction with specialized surgical instrumentation to detect, diagnose, and repair areas of the body that were previously only able to be repaired using traditional "open" surgery. In conjunction with the advances in endoscopic surgery, there have been many attempts to simplify the task of driving a needle carrying suture through body tissues to approximate, ligate and fixate them. Many prior disclosures, such as described in U.S. Pat. No. 919,138 to Drake et al., employs a hollow needle driven through the tissue with the suture material passing through the hollow center lumen. The needle is withdrawn, leaving the suture material in place, and the suture is tied, completing the approximation. A limitation of these types of devices is that they are particularly adapted for use in open surgical procedures where there is ample room for the surgeon to manipulate the instrument.

Others have attempted to devise suturing instruments that resemble traditional forceps, such as U.S. Pat. No. 3,946,740 to Bassett. These devices pinch tissue between opposing jaws and pass a needle from one jaw through the tissue to the other jaw. Graspers then pull the needle and suture material through the tissue. A limitation of these designs is that they also are adapted primarily for open surgery, in that they require exposure of the tissues to be sutured in order that the tissue may be grasped or pinched between the jaws of the instrument. This is a severe limitation in the case of endoscopic surgery.

Less invasive arthroscopic techniques are beginning to be developed in an effort to address the shortcomings of open surgical repair. Access to the operative site using endosurgical or minimally invasive techniques is accomplished by inserting small tubes, known as trocars, into a body cavity. These trocars have a diameter of, for example, between 3 mm and 30 mm and a length of about 150 mm (6 inches). Working through small trocar portals that minimize disruption of the deltoid muscle, surgeons have been able to reattach the rotator cuff using various bone anchor and suture configurations. The rotator cuff is sutured intracorporeally using instruments and techniques such as those previously described. The repair is completed by tying the cuff down against bone using the anchor and suture that is knotted to secure the tissue in proximity to the bone.

The suture knots in the tissue can be bulky and create a painful impingement of the tendon on the bone. This is because the knots end up on top of the cuff, in the sub-acromial space, and have the opportunity to rub on the acromion as the arm is raised. Because non-absorbable suture materials are used for these types of repairs, the suture and associated knots are not absorbed into the body, and hence provide a constant, painful reminder of their presence. Accordingly, devices configured to place, retrieve, and secure sutures in tissue without reliance on tying knots are desirable. Additionally, devices configured to grasp and secure tissue to effect the placement of suture in a particular location of the tissue provide an advantageous utility that is valued by practitioners during the practice of endoscopic tissue repair.

SUMMARY

The present device and methods include an instrument that combines the function of both grasping the tissue and passing sutures through the tissue to form a stitch. In a general sense, the instrument includes a pair of grasping jaws that oppose each other along a line substantially perpendicular to the long axis of the instrument. The distal end of the instrument incorporates the fixed jaw, and proximal to that jaw is a moveable jaw that is controlled by the user via a lever on the handgrip.

In a preferred embodiment the instrument is inserted through a portal known as a trocar cannula. The portal is created by first making an incision in the skin, and then inserting a cannula through the incision to the repair site. The distal end of the instrument is inserted through the cannula under direct visualization from a second trocar cannula that has been previously inserted. The visualization is accomplished via an endoscope, of a type well known in the art. The instrument is inserted until the jaws reach, for example, torn rotator cuff tissue. In operation, the distal end of the grasper aspect of the instrument is positioned at the repair site underneath the tissue to be grasped. The moveable jaw is movable toward the stationary jaw by squeezing the handle lever. The handle lever moves inward by pivoting about a pivot pin.

Once the surgeon is satisfied with the placement of the grasper on the grasped tissue, the surgeon can then deploy a suture needle to create a stitch in the tissue, for example, the above-mentioned torn rotator cuff. In operation, the suture needle may be advanced through the grasped tissues by actuating a second lever. In order to create the suture, at least one needle advances to engage a suture disposed in the stationary jaw. The needle comprises a distal point, a proximal shaft, and a hook defining a suture holding area. The suture needle is actuated such that the tip of the suture needle engages a portion of suture housed in a more distal portion of the stationary jaw, and begins to penetrate through the bottom of the grasped tissue and advances upward toward the movable jaw. Thereby, the device includes features to allow the needle engage and capture the suture and then to penetrate tissue and draw the suture through the tissue.

The movable jaw may incorporate a suture capture member disposed at a distal end of the device. In certain embodiments, the suture capture member may comprise a cartridge removably disposed on one of the jaws at the distal end of the distal. The suture capture member may be characterized by apertures coaxial to the longitudinal axis of the suturing device designed to allow the suture needle engaged with suture to pass therethrough. The suture capture member comprises components designed to spring away from the aperture in order to allow passage of the suture needle and suture through the aperture on the upstroke of the needle through the tissue. The aperture may be further characterized by opposed serrated edges, fingers or teeth to assist in securing the portion of suture as the needle begins a down stroke through the aperture and the tissue.

The instrument can be retracted back through the portal via the trocar cannula. As the instrument is removed from the suture site, the free ends of the suture are retrieved as well. This causes the suture form a looped stitch in the tissue.

Thus, the disclosed embodiments comprise a combination of features and characteristics which are directed to allow it to overcome various shortcomings of prior devices. The various characteristics described above, as well as other features, will be readily apparent to those skilled in the art upon reading the following detailed description of the preferred embodiments of the invention, and by referring to the accompanying drawings.

DETAILED DESCRIPTION

The present invention relates to a method and apparatus for suturing of soft tissue at a surgical repair site. In one variation the invention uses a device that is a combination tissue grasper and suture placement device. Although the present invention is described primarily in conjunction with the repair of a torn rotator cuff, the apparatus and method could also be used in arthroscopic repair at other sites, such as the knee, elbow, hip surgery, and for other surgical techniques for securing suture in the soft tissues of the body.

Figure 1:
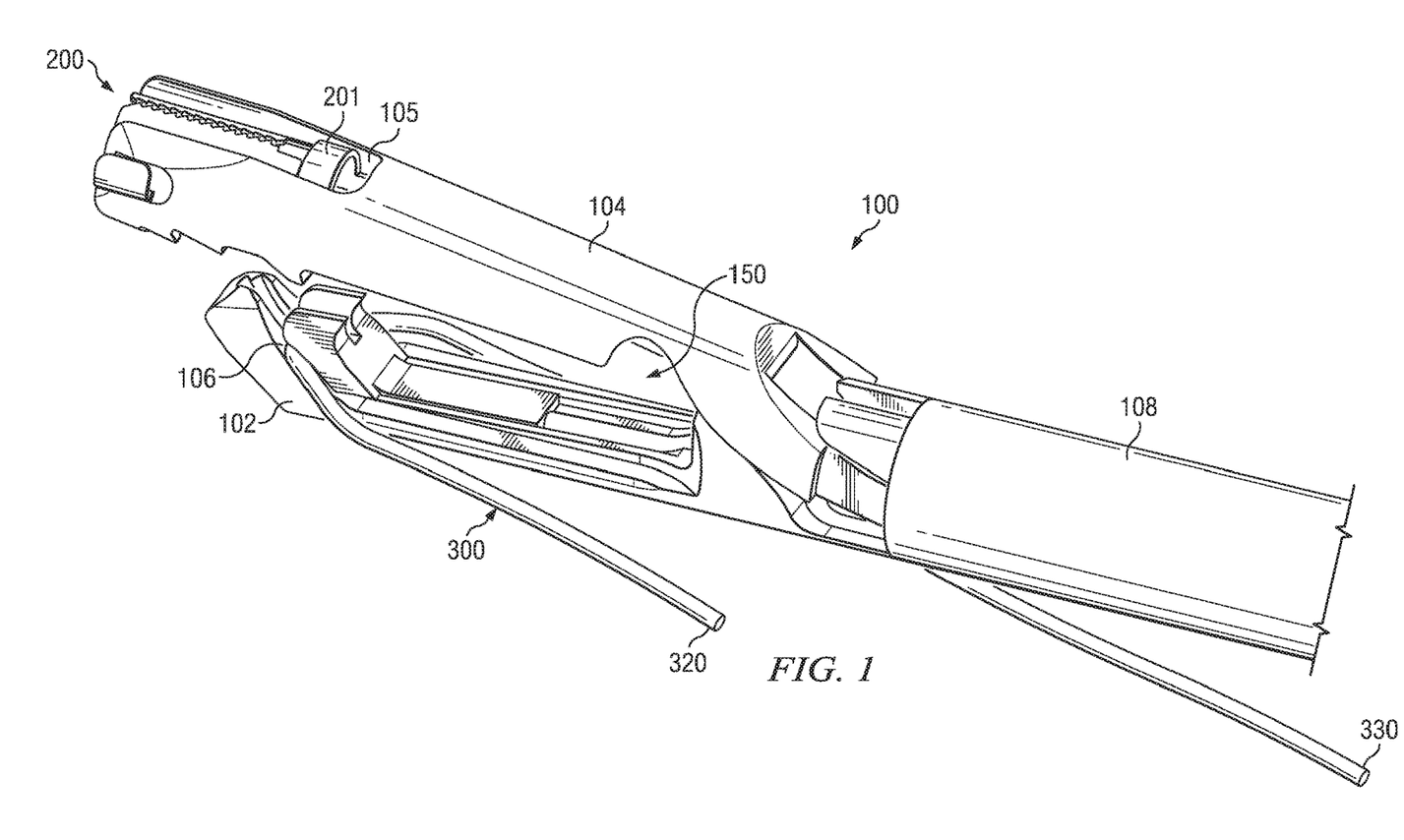
FIG. 1 illustrates a perspective view of a suturing device in accordance with at least some embodiments.

One embodiment of a suture passer instrument having a suture capture mechanism is shown in the perspective view of FIG. 1. Suturing device 100 includes lower jaw member 102 and upper jaw member 104 disposed at a distal end of the device. Jaws 102 and 104 are connected to an elongate housing 108 comprising a hollow tube. In certain embodiments, upper jaw 104 may be further characterized by opening 105 at the distal end of device 100. Lower jaw 102 may have a suture recess 106 oriented in a generally perpendicular direction to the longitudinal axis of device 100 for engaging and accommodating a length of suture 300 with free ends 320, 330 in preparation for stitching the length of suture 300 through the soft tissue and subsequently capturing the length of suture 300. The distal portion of device 100 between jaws 102, 104 defines a tissue receiving area 150.

Figure 2A:
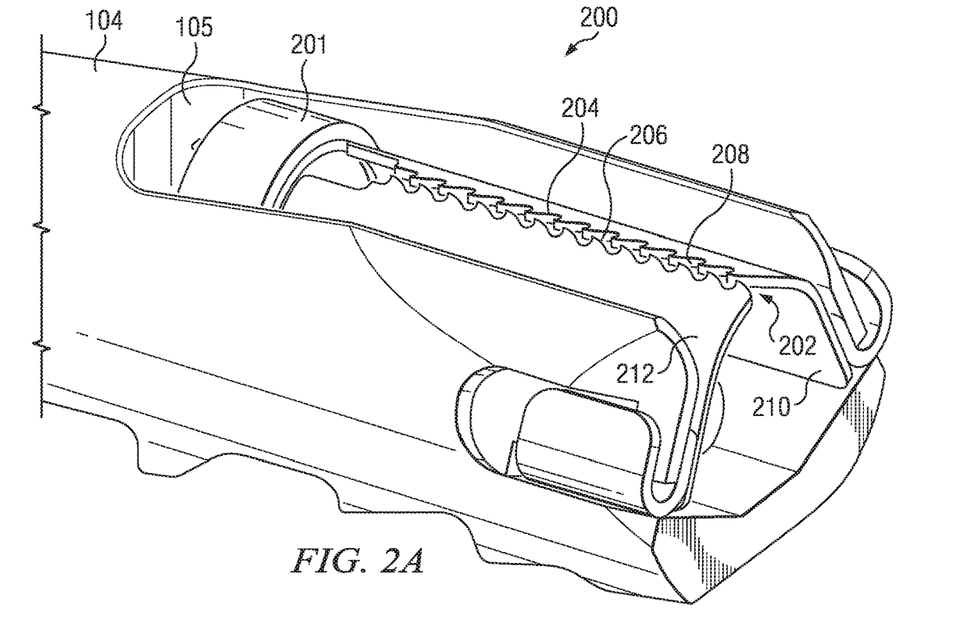
FIG. 2A illustrates a perspective view of a suture capture member in accordance with at least some embodiments.
Figure 2B:
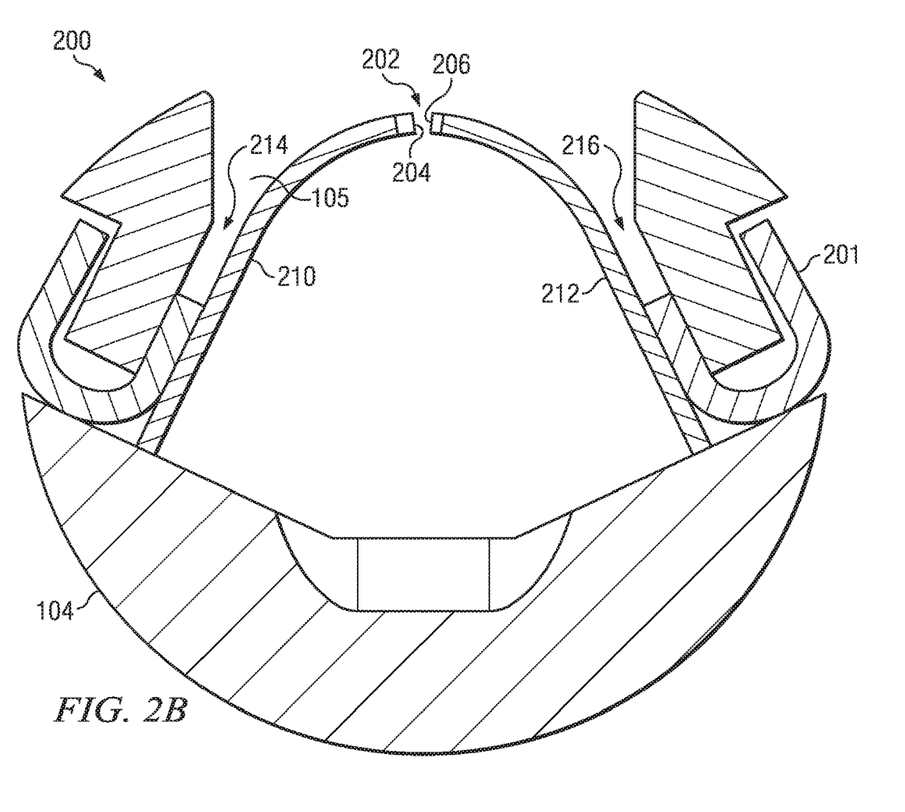
FIG. 2B illustrates a cross-sectional view of the suture capture member in accordance with at least some embodiments.
Figure 3:
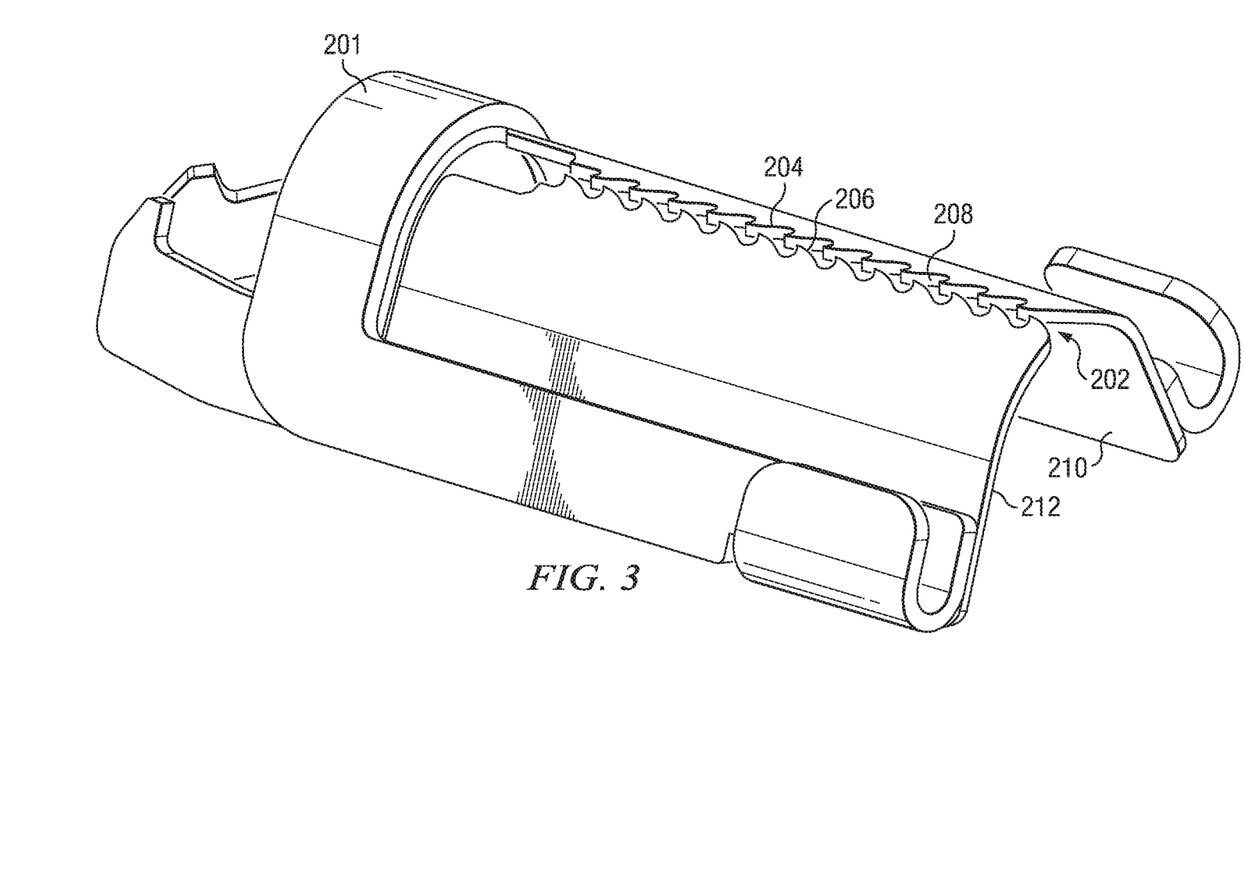
FIG. 3 illustrates a perspective view of a suture capture cartridge in accordance with at least some embodiments.

In certain embodiments, upper jaw 104 includes suture capture member 200 disposed at the distal end of device 100. Suture capture member 200 may in some embodiments comprise a suture capture cartridge 201 removably disposed within opening 105 of upper jaw 104. Referring now to FIGS. 2A and 3, suture capture member 200 comprises elongate aperture 202 formed by edges 204, 206 on each opposed side. Edges 204, 206 may further comprise suture capture surface 208 in certain embodiments. Suture capture surface 208 may be configured as opposed serrated edges, a plurality of interdigitating teeth, a plurality of opposed notches, or other similar opposed edge features. Suture capture cartridge 200 further comprises deflecting portions 210, 212 (i.e., arms 210, 212) which extend from edges 204, 206 respectively, and may be formed in a curved or arcuate shape. Referring now to FIG. 2B, suture capture member 200 is disposed relative to upper jaw 104 such that gaps 214, 216 are created between arms 210, 212 and the respective inner surfaces within upper jaw 104. In certain embodiments, cartridge 201 and/or the components of suture capture member 200 are preferably comprised of high temper spring steel material.

Figure 4A:
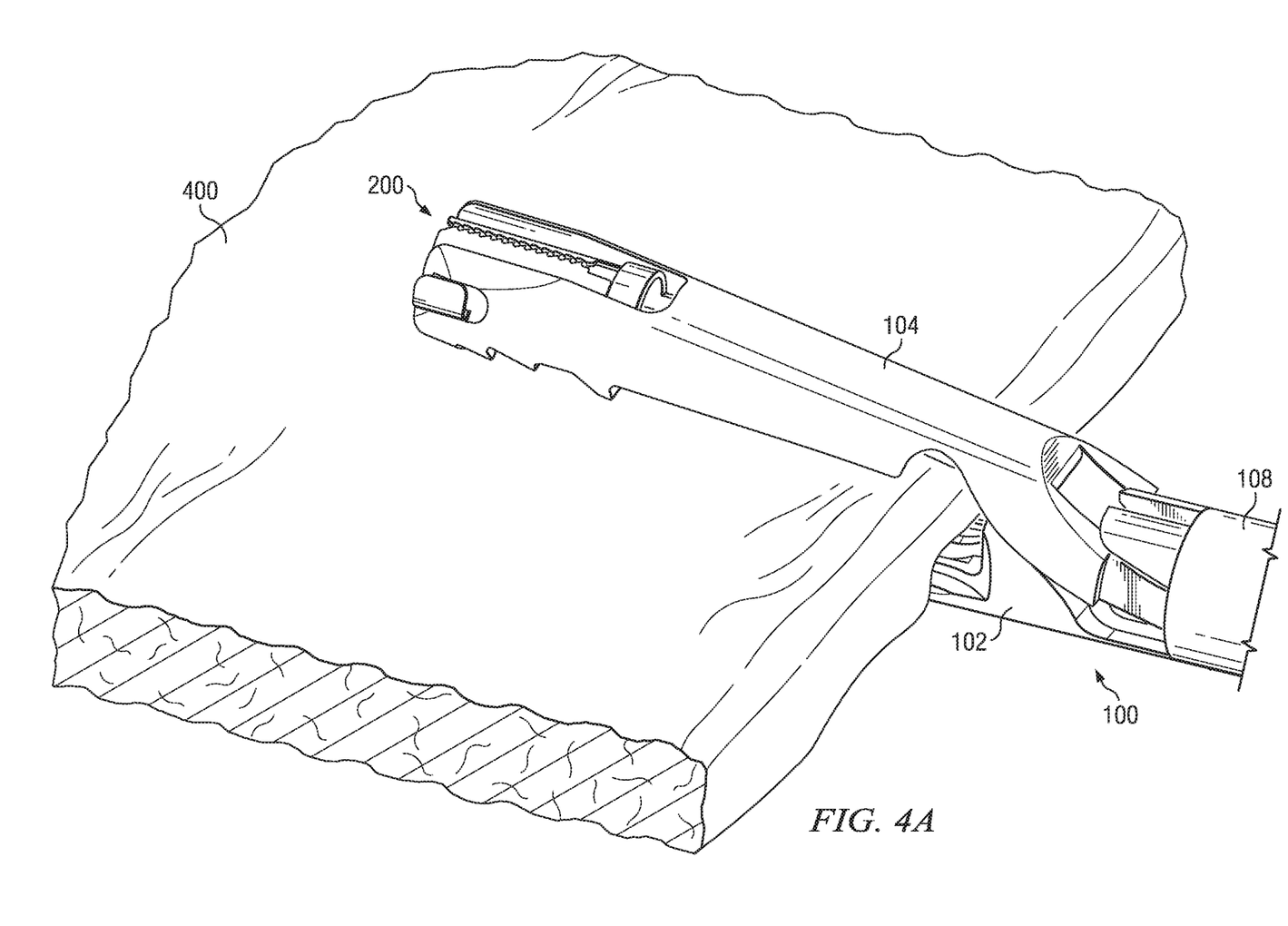
FIG. 4A illustrates a perspective view of a suturing device in accordance with at least some embodiments.

Suturing device 100 is inserted through a trocar cannula until jaws 102, 104 reach the tissue to be treated. Upper jaw 104 may be actuated into the open configuration and soft tissue 400 is introduced into the space between the upper jaw 104 and the lower jaw 102. Referring now to FIG. 4A, by means of a mechanism not discussed or shown herein, but of a type well known to those skilled in the art, the upper jaw 104 is movable relative to lower jaw 102, causing upper jaw 104 to clamp or grasp the soft tissue 400 and immobilize it between the upper jaw 104 and the lower jaw 102. In certain embodiments, upper jaw 104 may be pivoted about a generally perpendicular axis relative to housing 108, or alternatively the connection between lower jaw 102 and upper jaw 104 may be a reciprocating or cam system wherein upper jaw 104 is movable relative to lower jaw 102. With upper jaw 104 positioned in proximity to lower jaw 102, jaws 102, 104 are thereby positioned in the closed configuration.

Figure 4B:
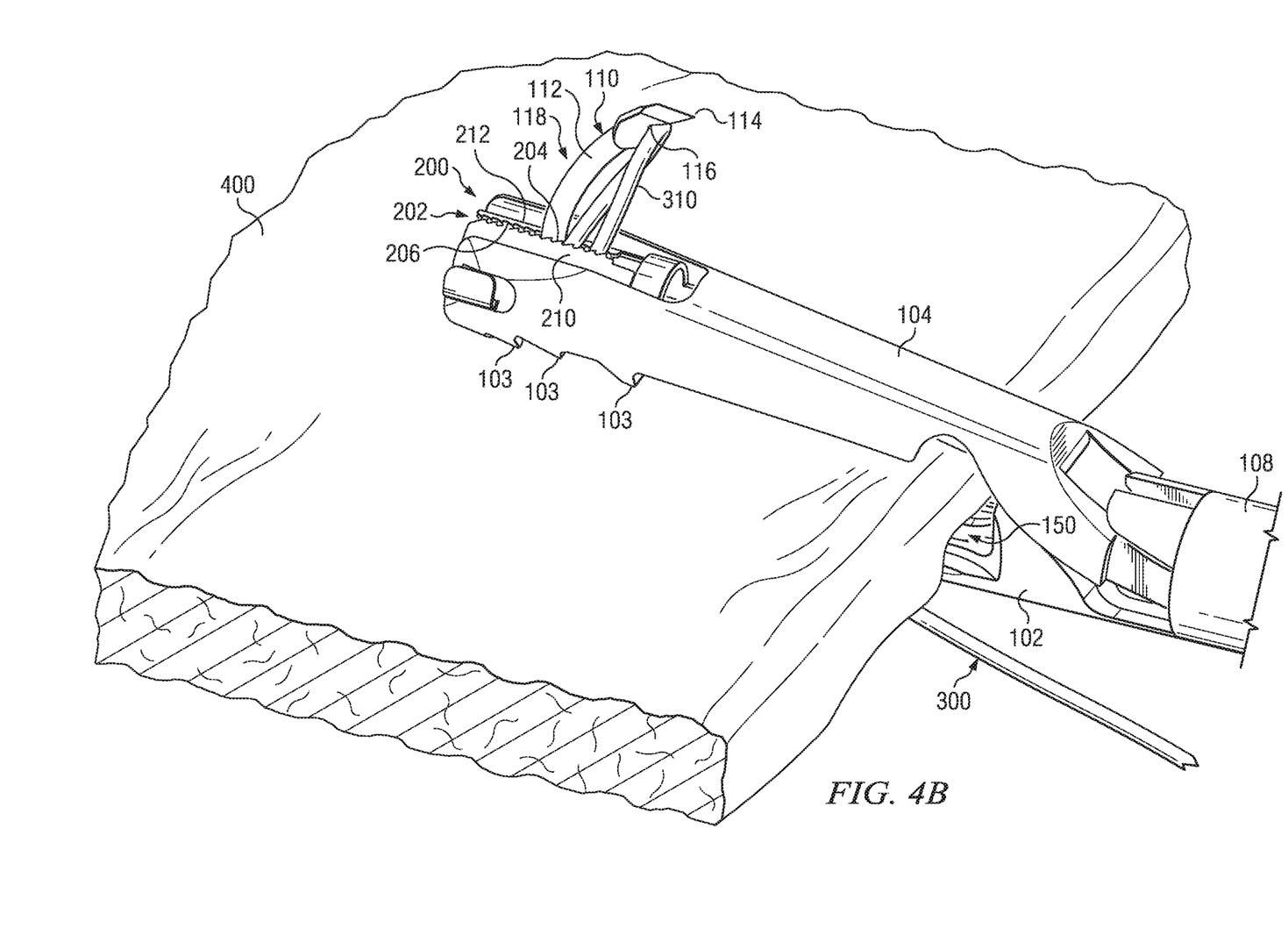
FIG. 4B illustrates a perspective view of a suturing device in accordance with at least some embodiments.

In certain embodiments, lower jaw 102 is stationary while upper jaw 104 is movable relative to lower jaw 102 or pivotable about a fixed point coupled to the distal end of housing 108. The movable nature of upper jaw 104 allows jaws 102, 104 to be actuated between an open configuration for receiving tissue and a closed configuration for grasping tissue. Referring now to FIG. 4B, suture needle 110 is movably disposed within housing 108, and comprises shaft 112, point 114, and suture capture area 116. Needle 110 is axially movable within and extendable from housing 108, such that needle point 114 may be positioned in a retracted position withdrawn from tissue receiving area 150 or in an extended position displaced through upper jaw 104. According to the embodiments described herein, needle 110 is configured such that it is generally directable upward from its retracted position away from tissue receiving area 150 to its extended position displaced through upper jaw 104 and soft tissue 400. For example, it is contemplated that needle 110 may be ramped generally upward off a surface in lower jaw 102 as it is displaced from the retracted position to the extended position. In certain embodiments, needle 110 is comprised of a super-elastic material such as nitinol, has a generally circular cross-section, and is preformed to include a bend or curved region 118 at the distal end portion of needle 110. The super-elastic nature of the material comprising needle 110 in these embodiments allows that needle 110 may be disposed in a generally linear configuration while placed in the retracted position, and then returns to the preformed curved configuration during the displacement of needle 110 from the retracted to extended position.

The housing 108 is coupled to a handle portion (not shown) having a similar or the same design as those typically used in conventional suturing devices as discussed above. For example, such a handle portion in accordance with the embodiments discussed herein may have a stationary grip with a moveable needle deployment lever to actuate axial movement of the needle. The handle portions further include a deployment member or trigger to effectuate closing of the jaws 102, 104 to grasp and secure the tissue therebetween.

With the position of the soft tissue 400 grasped between jaws 102, 104 and within the tissue receiving area 150 device 100 deemed satisfactory, needle 110 may be deployed by actuation of needle deployment member or trigger in the handle portion of device 100 to the extended position, as depicted in FIG. 4B. Needle 110 is advanced axially toward the distal end of device 100 such that suture capture area 116 engages suture 300 accommodated in suture recess 106 of lower jaw 102 (as previously described and depicted in FIG. 1). As described above, in certain embodiments needle 110 comprises a super-elastic material and is preformed to include a bend or curved region 118. The preformed curved region 118 of needle 110 allows that as needle 110 is advanced in a generally distal direction needle point 114 is urged toward upper jaw 104 and needle point 114 thereby penetrates and enters the underside of soft tissue 400 grasped between jaws 102, 104. In addition to needle point 114 penetrating and entering soft tissue 400, the advancement of needle 110 also results in passing suture capture area 116 and the length of suture 300 engaged within suture capture area 116 through soft tissue 400. The tissue receiving area 150 may be defined by protrusions or teeth 103 to assist in retaining the tissue within the tissue receiving area 150 as needle 110 advances through the soft tissue 400.

With needle point 114, suture capture area 116, and suture 300 drawn through soft tissue 400, the actuation of needle 110 continues until needle 110 advances into and through opening 105 in upper jaw 104. Concurrently, needle 110 and length of suture 300 are also directed through aperture 202 of suture capture member 200. Referring concurrently to FIGS. 2B and 4, as needle 110 passes through aperture 202, needle 110 contacts edges 204, 206 such that each of arms 210, 212 are deflected away from needle 110 and into a portion of gaps 214, 216. The deflection of arms 210, 212 is designed to be elastic such that arms 210, 212 respectively return to or spring back into a pre-deflected position upon the subsequent withdrawal of needle 110 through aperture 202. In the fully extended position of needle 110, the length of suture 300 that has been drawn through soft tissue 400 forms a suture portion 310 which protrudes from and is disposed above upper jaw 104 and suture capture member 200. In certain embodiments, suture portion 310 may form a looped configuration.

Figure 4C:
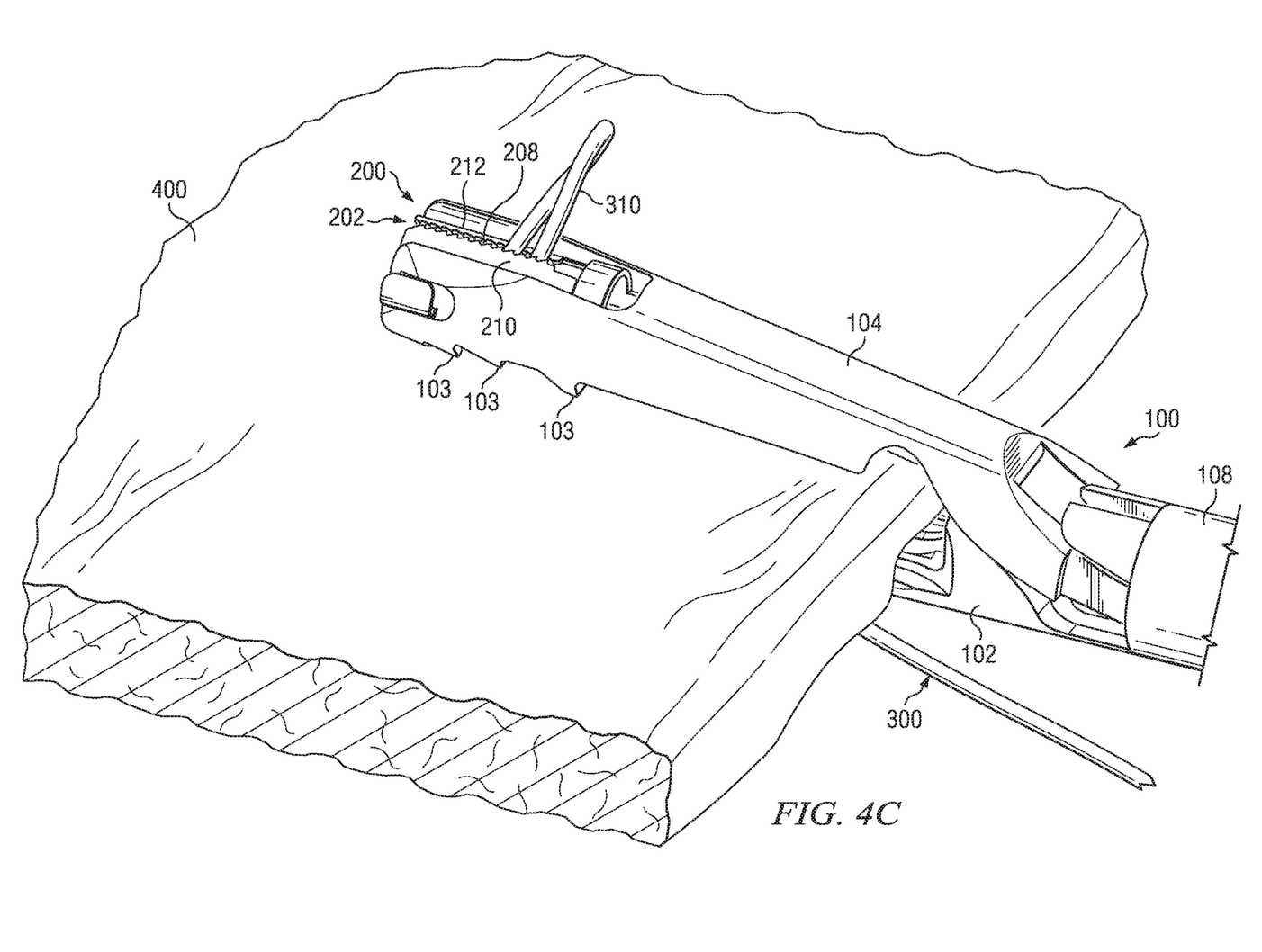
FIG. 4C illustrates a perspective view of a suturing device in accordance with at least some embodiments.

With the suture portion 310 protruding through suture capture member 200, needle 110 may be withdrawn through aperture 202 and returned to a retracted position, as depicted in FIG. 4C. As needle 110 is withdrawn through suture capture member 200, arms 210, 212 spring back to a non-deflected position such that aperture 202 and suture capture surface 208 are allowed to close around suture portion 310 of suture 300. Aperture 202 is large enough and the spring deflection of arms 210, 212 is great enough that these characteristics of suture capture member 200 do not restrict the movement of needle 110 during displacement to the extended position. However, arms 210, 212 are configured such that arms 210, 212 can only be deflected in an outward direction, away from the top outer surface of upper jaw 104, as needle 110 is moved through aperture 202 during displacement to the extended position. In addition, aperture 202 is sufficiently small when arms 210, 212 are in the non-deflected configuration so that suture portion 310 is not allowed to pass back through suture capture member 200. Further, suture capture surface 208 engages and captures suture portion 310, and further secures suture portion 310 of suture 300 as needle 110 is withdrawn through aperture 202 and returned to the retracted position. Thereby, suture portion 310 is trapped in suture capture member 200 on upper jaw 104 with a portion of suture 300 simultaneously stitched through soft tissue 400. Thereafter, jaws 102, 104 of device 100 are opened to release soft tissue 400 from the grasp of device 100.

Figure 4D:
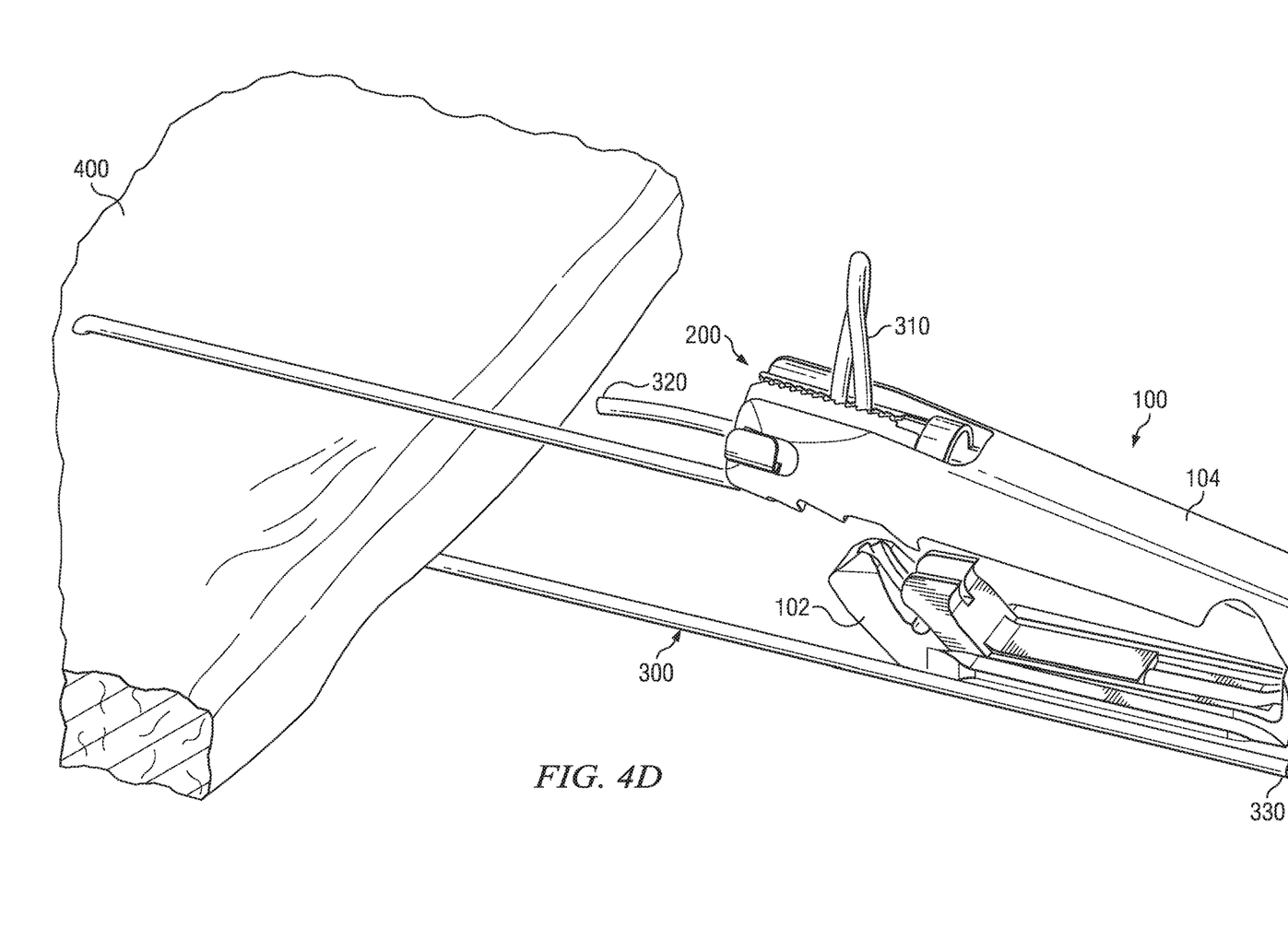
FIG. 4D illustrates a perspective view of a suturing device in accordance with at least some embodiments.

Referring now to FIG. 4D, with jaws 102, 104 of device 100 fully actuated into the open configuration and needle 110 displaced to the fully retracted position (not shown), device 100 is pulled away from the repair site and retracted through the trocar cannula, thereby leaving a portion of suture 300 stitched through a portion of soft tissue 400. Concurrently, suture portion 310 of suture 300 may be pulled away from the repair site and withdrawn from the trocar cannula. Suture portion 310 is manually removed from suture capture member 200 creating suture free ends 320, 330 that may be utilized to secure soft tissue 400 to a desired location using soft tissue attachment methods or bone anchors otherwise known in the art.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A suturing device for use endoscopically comprising:
   a first and second jaw member disposed at a distal end of the device;
   a needle disposed in the first jaw member while in a retracted position and movable between the retracted position and an extended position, the needle operable to selectively engage a length of suture; and
   a suture capture member disposed on the second jaw member, wherein the suture capture member defines a spring, a proximal fixed end and a free distal edge; wherein moving the needle to the extended position is configured to spring load the suture capture member, and angularly move the free distal edge, and wherein retraction of the needle releases the suture capture member to spring back and capture the length of suture within the suture capture member.

2. The device of claim 1, wherein the first jaw member comprises a suture recess configured to engage the length of suture while the needle is in the retracted position.

3. The device of claim 1, wherein extending the needle comprises moving the needle axially in a distal direction.

4. The device of claim 1, wherein the suture capture member is a suture capture cartridge removably disposed on the second jaw member.

5. The device of claim 1 wherein the second jaw is configured to move relative to the first jaw and grasp tissue.

6. The device of claim 1 wherein the suture capture member defines an elongate gap between an inner surface of the second jaw member and an outer surface of the suture capture member, the suture capture member operable to be spring loaded into the elongate gap as the needle moves to the extended position.

7. The device of claim 1, wherein the suture capture member defines an aperture centrally disposed along the suture capture member and coaxial with a longitudinal axis of the suture device.

8. A suturing device for use endoscopically comprising:
a first and second jaw member disposed at a distal end of the device;
a needle disposed in the first jaw member while in a retracted position and movable between the retracted position and an extended position, the needle operable to selectively engage a length of suture; and
a spring member disposed on the second jaw member, wherein the spring member defines a free distal end and a single suture capture aperture and is configured to be spring loaded as the needle enters the aperture and moves toward the extended position, moving the distal end away from a longitudinal axis of the device and wherein upon removal of the needle the spring member springs back towards a less spring loaded configuration such that a portion of the length of suture is captured by spring member and within the aperture.

9. The suture device of claim 8 wherein the spring member defines an elongate gap between an inner surface of one of the second jaw member and an outer surface of the spring member, the spring member operable to be deflected into the elongate gap as the needle moves to the extended position.

10. The device of claim 8, wherein the aperture that is centrally disposed along the jaw member and coaxial with a longitudinal axis of the suture device.

11. The device of claim 8 wherein the spring member defines an arm having a fixed proximal end the arm configured to angularly move relative to the second jaw as the spring member is spring loaded by the needle.

12. The device of claim 8 wherein the aperture extends up to and including a free distal-most edge of the spring member.

13. The device of claim 8 wherein the spring member comprises two arms, each having fixed proximal ends and free distal edges.

14. The device of claim 8, wherein the first jaw member comprises a suture recess, configured to selectively engage the length of suture as the needle moves from the retracted portion to the extended position.

15. The device of claim 14 wherein the suture recess is configured to selectively receive the needle therethrough as the needle moves towards the extended configuration.

16. The device of claim 8, wherein extending the needle comprises moving a suture capture area of the needle axially in a distal direction.

17. The device of claim 8, wherein the spring member comprises a suture capture cartridge removably coupled to the second jaw member.

18. A suturing device for use endoscopically comprising:
a first and second jaw member disposed at a distal end of the device;
a needle disposed in the first jaw member while in a retracted position and movable between the retracted position and an extended position, the needle operable to selectively engage a length of suture; and
a spring member disposed on the second jaw member, the spring member defining at least a portion of a suture capture aperture and having a free distal-most edge, and wherein the spring member is configured to deflect away from the needle and angularly move the free distal-most edge relative to the second jaw member as the needle extends through the suture capture aperture, and wherein upon removal of the needle the spring member springs back towards a less spring loaded configuration such that a portion of the length of suture is captured within the aperture.

19. The suturing device of claim 18 wherein the free distal-most edge is configured to angularly move away from the first jaw as the needle extends through the suture capture aperture.

* * * * *